US006732382B2

United States Patent
Dondero (10) Patent No.: US 6,732,382 B2
(45) Date of Patent: May 11, 2004

(54) GOGGLE FOR PROTECTING EYES WITH A MOVABLE VENT COVER AND METHODS FOR USING

(76) Inventor: John Dondero, P.O. Box 739, Sun Valley, ID (US) 83353

( * ) Notice: Subject to any disclaimer, the term of this patent is extended or adjusted under 35 U.S.C. 154(b) by 0 days.

(21) Appl. No.: 10/116,685

(22) Filed: Apr. 3, 2002

(65) Prior Publication Data

US 2003/0188376 A1 Oct. 9, 2003

(51) Int. Cl.⁷ .................................................. A61F 9/02
(52) U.S. Cl. ............................................. 2/436; 2/437
(58) Field of Search ........................... 2/12, 13, 15, 426, 2/428, 435, 436, 437, 438, 440, 441

(56) References Cited

U.S. PATENT DOCUMENTS

| | | | |
|---|---|---|---|
| 3,638,240 A | * 2/1972 | Militello | 2/14 |
| 4,977,627 A | * 12/1990 | Metcalfe et al. | 2/441 |
| 5,363,512 A | * 11/1994 | Grabos, Jr. et al. | 2/441 |
| 5,652,965 A | * 8/1997 | Crooks | 2/436 |
| 5,966,746 A | * 10/1999 | Reedy et al. | 2/436 |
| 6,138,285 A | * 10/2000 | Robrahn et al. | 2/436 |
| 6,233,342 B1 | * 5/2001 | Fernandez | 2/235 |

OTHER PUBLICATIONS

Nine (9) photographs of a Carrers goggle/mouth guard. The goggle/mouth guard was first publicly used in the United States before Apr. 3, 2001.

* cited by examiner

Primary Examiner—Gary L. Welch
(74) Attorney, Agent, or Firm—Graybeal Jackson Haley, LLP (57) ABSTRACT

A goggle comprising a lens, a frame and a vent cover including an attachment component and a retention component, wherein the vent cover can be selectively moved relative to the frame to at least two different positions defining substantially different levels of airflow through frame vents, and retained at each position. In certain embodiments, one position is defined by substantially all of the peripheral-contact surface of the vent cover contacting the frame wherein a first level of airflow can be either substantially non-zero or substantially zero. Other positions are defined by substantially all of the peripheral-contact surface not contacting the frame wherein outside air is allowed to flow across the inside surface of the lens. In certain embodiments, the attachment component comprises a tongue that is inserted into a vent-cover attachment hole in the frame, and the retention component comprises a retention post insertable into vent-cover retention holes in the frame and guide posts inserted into guide slots in the frame. The attachment component and retention component may be the same component.

9 Claims, 3 Drawing Sheets

GOGGLE FOR PROTECTING EYES WITH A MOVABLE VENT COVER AND METHODS FOR USING

BACKGROUND

Goggles, masks and other eye-protection systems are very useful to keep dust, wind, gravel, metal shavings and the like out of the eyes. In humid environments and/or during strenuous physical activity a great deal of ventilation between the lens of the goggle or masks and the eyes of the user is highly preferable to prevent or remove condensation from inside the goggles, masks or other systems. In other situations where dust, metal shavings or the like can easily irritate the eyes, a substantially complete seal and/or a partial or filtered seal between the lens and the eyes of a user is desirable.

Unfortunately, in order to vary the amount of ventilation between the lens and eyes of a user, the user typically needs to remove the particular goggle, mask or eye-protection system and put on a different pair. This is expensive because the user needs several different goggles, masks, lenses, etc., and inconvenient because the user must stop whatever they are doing (for example, skiing, snowboarding, motorcycle racing, performing a rescue, etc.) to change the goggle, mask and/or lens. Thus, there has gone unmet a need for a goggle, mask and/or lens that is capable of providing a plurality of different ventilation states while maintaining substantial eye protection in each ventilation state.

The present invention provides goggles that comprise a vent cover which can be set at a plurality of different positions relative to the frame of the goggle, mask or glasses, so that a plurality of different ventilation states are possible while the lens is maintained in front of at least one eye of a user. The present invention additionally provides other advantages.

SUMMARY

The present invention provides goggles and methods comprising a vent cover that can be selectively moved relative to a frame to increase and/or decrease ventilation of the goggle. Typically, the vent cover can be moved with or without gloves on the user's hands, and can be permanently or removably attached to the frame. Such goggles and methods are desirable, for example during strenuous activities including sports, technical rescues or military operations, because they make it easy to remove moist air from the enclosed environment between the user's eyes and the lens, yet can substantially prevent dust and debris or the like from injuring the user's eyes.

Thus, in one aspect, the invention provides a goggle comprising a lens attached to a frame that is sized to maintain the lens in front of at least one eye of a user. The lens and frame define an interior region, the region in front of at least one eye of a user enclosed by the lens and frame when the goggle is worn by the user, and an exterior region, the region outside the goggle when the goggle is worn by a user. The frame comprises frame vents comprising at least two of the group consisting of a top frame vent, a bottom frame vent and a side frame vent that define a passage operable to transmit air between the interior region and the exterior region and facilitate cross ventilation of a portion of the goggle. The goggle also comprises a vent cover adjustably attached to the frame by an attachment component and retention component, and moveable relative to the frame between a first position defining a first level of airflow through the frame vents and a second position defining a second, substantially greater level of airflow through the frame vents. For example, the first position can be defined by a first level of airflow that is substantially zero, and the second position can be defined by locating a peripheral-contact surface of a vent cover a first, substantially constant distance away from a frame-vent perimeter of a frame vent. The goggle can further include a vent cover that can be adjustably attached to and moveable relative to the frame to a third or more positions providing different levels of airflow, if desired.

Embodiments of the goggle include various embodiments of the frame. The frame can comprise a left side and a right side. The goggle can comprise a first vent cover adjustably attached to and moveable relative to the left side of the frame and a second vent cover adjustably attached to and moveable relative to the right side of the frame. Additionally or alternatively, the frame can comprise a top frame vent in a top portion of the frame and a bottom frame vent in a bottom portion of the frame that facilitate cross ventilation of a portion of the interior region when the vent cover is in a position that permits airflow through the top and bottom frame vents. In other embodiments, the frame can comprise a top, bottom and side frame vents in respective top, bottom and side portions of the frame. Additionally or alternatively, the frame can comprise at least one of the frame vents covered by a filter element to allow filtered airflow into the interior region when the vent cover is in a position that permits airflow through the covered frame vent.

Embodiments of the goggle include various embodiments of the vent cover. For example the vent cover can comprise a body, a top cover portion and bottom cover portion that extend from the body and include a peripheral-contact surface, an attachment component to adjustably attach the vent cover to a frame of a goggle, and a retention component to retain the vent cover in at least a first and second position relative to the frame when the vent cover is attached to the frame. In some embodiments of the vent cover, the top and bottom cover portion can extend from the body such that the vent cover is substantially U-shaped. Additionally, the vent cover can further comprise a side cover portion.

Embodiments of the vent cover include various embodiments of the cover portions. For example, one or more cover portions can comprise a cover vent corresponding to and aligned with a frame vent in the frame. The cover vent can be covered by at least one of the group consisting of a membrane and a filter element. When the cover vent is covered by a filter element and the vent cover is in the first position, filtered air can flow through the cover vent and corresponding frame vent to ventilate the interior region. When the cover vent is covered by a membrane and the vent cover is in the first position, the first level of airflow can be substantially zero. Furthermore, if the corresponding frame vent is covered by a filter element and the vent cover is in the second or other position, a substantially greater level of filtered air can flow through the frame vent to ventilate the interior region.

Embodiments of the vent cover include various embodiments of the attachment and retention components. For example, the attachment component can comprise a tongue extending from the vent cover that slides within a vent-cover attachment hole in the frame that is sized to receive the tongue. Additionally, the attachment component can include a lip sized and located on a tongue to substantially prevent the tongue from sliding out of the vent-cover attachment hole in the frame.

The retention component, for example, can comprise a retention post extending from the vent cover and sized to fit into at least first and second vent-cover retention holes in the frame. The first and second vent-cover retention holes are located in the frame so that when the retention post is inserted into the first hole, the vent cover is in the first position, and when the retention post is inserted into the second hole, the vent cover is in the second position. The retention component can also comprise a guide post extending from the vent cover and sized to fit into and slide within a guide slot in the frame.

In another aspect, the invention provides a method for ventilating a goggle that comprises placing the vent cover of a goggle in a first position relative to a frame of the goggle, the frame comprising frame vents comprising at least two of the group consisting of a top frame vent, a bottom frame vent and a side frame vent, the first position permitting a first level of airflow through each frame vent, moving the vent cover relative to the frame to a second position that permits a second level of airflow through each frame vent, wherein the second level of airflow is substantially greater than the first level of airflow. In some executions of the method, the method can further comprise retaining the vent cover in at least one of the positions. For example, the vent cover can be retained in one of the positions by inserting a retention post of the vent cover into a vent-cover retention hole in the frame. In these and other executions of the method, placing and moving the vent cover can be performed while a user of the goggle is strenuously physically active. In addition, in these and other executions of the method, moving the vent cover can comprise a) pushing or pulling the vent cover with at least one of the user's hands and b) sliding a tongue of the vent cover within a vent-cover attachment hole in the frame.

These and other aspects, features and embodiments are set forth within this application, including the following Detailed Description and attached drawings. The present invention comprises a variety of aspects, features and embodiments; such multiple aspects, features and embodiments can be combined and permuted in any desired manner.

DETAILED DESCRIPTION

The present invention provides goggles and methods comprising a vent cover that is selectively moved between at least two different positions relative to a frame to increase and/or decrease ventilation of the goggle. For example, the vent cover can be moved to increase cross ventilation to efficiently ventilate the goggle. A first position defines or permits a first level of airflow between an exterior region, the region outside the goggle when the goggle is worn by a user, and an interior region of the goggle, the region in front of at least one eye of a user enclosed by the lens and frame when the goggle is worn by the user. A second position defines or permits a second, substantially greater, level of airflow between the exterior and interior regions. The goggles and methods can further provide a third or more positions providing different levels of airflow, if desired. The goggles and methods allow the lens to remain in front of the eyes of the user in each of the various positions to protect the eyes of the user as the user increases or decreases ventilation of the interior region. To adjustably attach the vent cover to the frame, the vent cover can, for example, comprise an attachment component. To retain the vent cover in the first and other positions, the vent cover can, for example, comprise a retention component. The goggles can comprise one, two, or more vent covers. In one of the positions, the vent cover can cover two or more frame vents or a fraction or portion of one or more of the frame vents. In some embodiments, if desired, the attachment component can also be the adjustment component and vice-versa.

Such goggles and methods are desirable because they maintain the lens in front of at least one eye of the user while permitting different levels of air flow between the exterior and interior regions. This can permit a user to choose how much air reaches his or her eyes, and can permit the user to cross ventilate the goggles, both during periods of strenuous physical activity and during periods of rest—even though the user may be perspiring during such rest periods or moving from a cold area to a warm area that normally would fog the lens. In other words, the goggles and methods are desirable during strenuous physical activities that can include sports, firefighting, performing rescues or performing military operations, and are desirable in industrial labor environments such as metal or wood working shops or in other physically demanding environments, because they facilitate the removal of moist air from the interior region between the user's eyes and the goggle's lens and yet protect the user's eyes from wind, dust, debris or the like.

The scope of the present invention includes both means plus function and step plus function concepts. However, the terms set forth in this application are not to be interpreted in the claims as indicating a "means plus function" relationship unless the word "means" is specifically recited in a claim, and are to be interpreted in the claims as indicating a "means plus function" relationship where the word "means" is specifically recited in a claim. Similarly, the terms set forth in this application are not to be interpreted in method or process claims as indicating a "step plus function" relationship unless the word "step" is specifically recited in the claims, and are to be interpreted in the claims as indicating a "step plus function" relationship where the word "step" is specifically recited in a claim.

All terms used herein, including those specifically described below in this section, are used in accordance with their ordinary meanings unless the context or definition indicates otherwise. Also unless indicated otherwise, except within the claims, the use of "or" includes "and" and vice-versa. Non-limiting terms are not to be construed as limiting unless expressly stated (for example, "including" and "comprising" mean "including without limitation" unless expressly stated otherwise).

Figure 1:
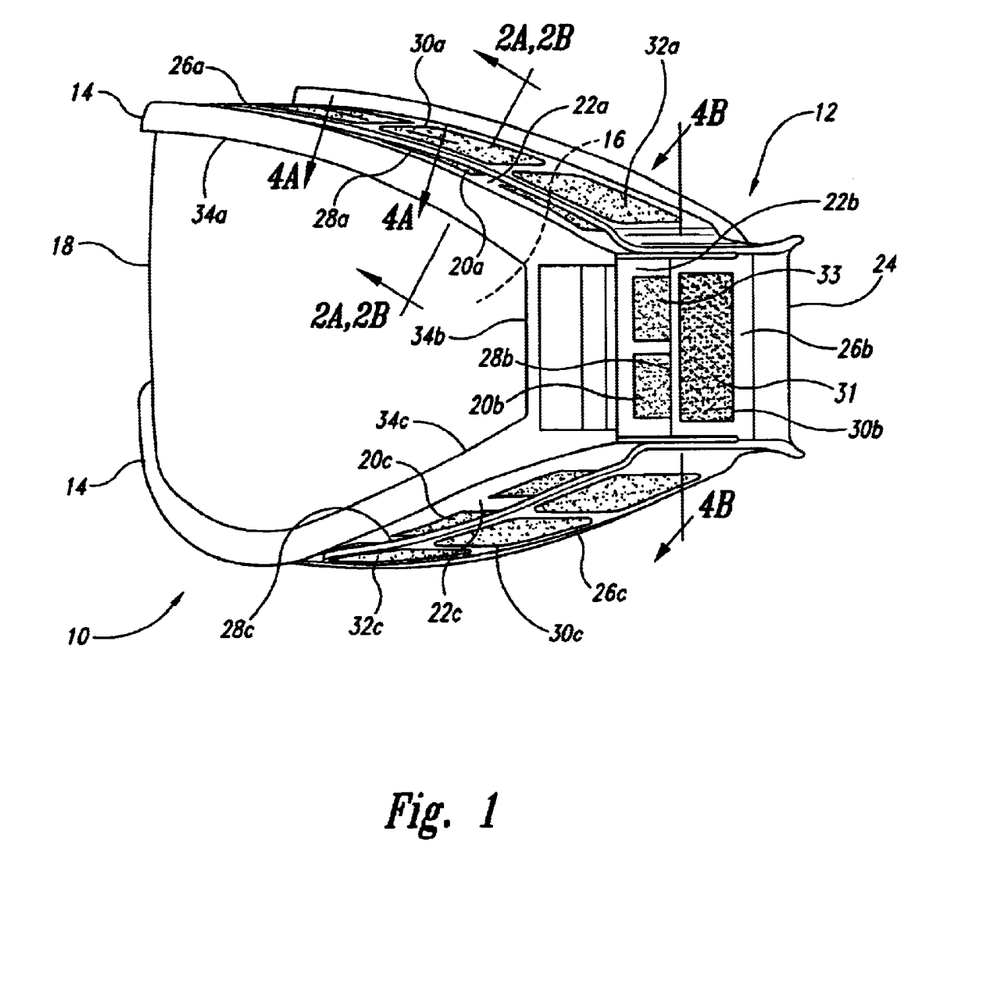
FIG. 1 is a side view of a goggle according to one embodiment of the invention.
Figure 2A:
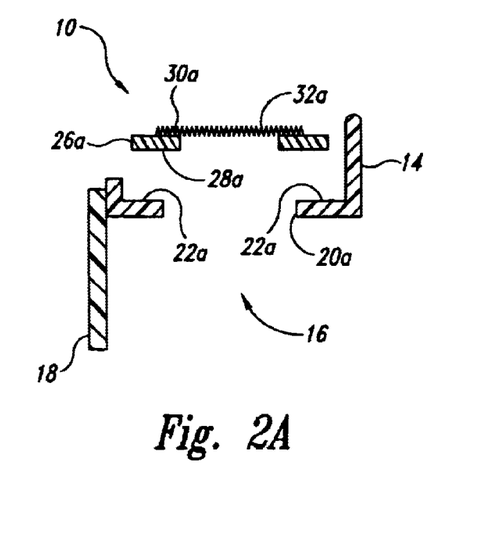
FIG. 2A is a partial cross-sectional view of the goggle of FIG. 1, illustrating the vent cover extended away from the frame to increase ventilation of the goggle.
Figure 2B:
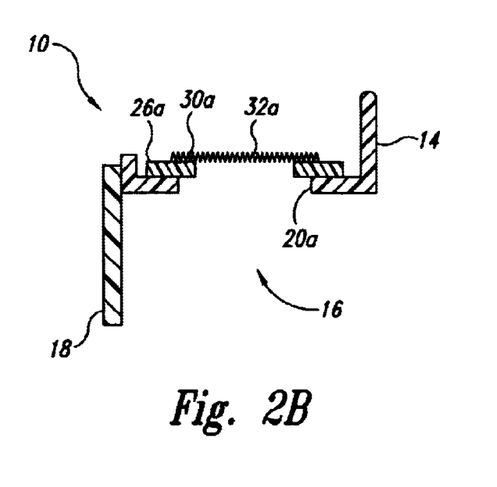
FIG. 2B is a partial cross-sectional view of the goggle of FIG. 1, taken at the same location as FIG. 2A, illustrating the vent cover retracted to the frame to decrease ventilation of the goggle.

Turning to the figures, FIGS. 1–2B illustrate a goggle 10 according to one embodiment of the invention. FIG. 1 is a side view of the goggle 10, and FIGS. 2A and 2B are partial cross-sectional views of the goggle 10 in FIG. 1 taken at the same location. FIGS. 1 and 2A illustrate a vent cover 12 retained in a position relative to a frame 14 that permits cross ventilation of a portion of the goggle and permits a substantially greater level of airflow between an exterior region (not shown) and an interior region 16 than the position illustrated in FIG. 2B that the vent cover 12 is retained in.

Referring to FIGS. 1–2B, the goggle 10 allows a user to quickly, easily and adjustably cross ventilate one or more portions of the goggle's interior region 16. In this and certain other embodiments, the goggle 10 comprises a lens 18 for protecting the eyes of a user, a frame 14 for maintaining the lens 18 in front of the user's eyes when the goggle 10 is worn by the user, and two vent covers 12 (only one shown) adjustably attached to the frame 14 and movable relative to the frame 14 to at least a first and second position. A first vent cover 12 is adjustably attached to a left side of the frame 14 while a second vent cover (not shown) is similarly adjustably attached to the right side (not shown) of the frame 14. The frame 14 comprises three frame vents 20a–20c, but can comprise one, two or more than three frame vents, and each frame vent 20a–20c comprises a corresponding frame-vent perimeter 22a–22c. The vent cover 12 comprises a body 24 and three cover portions 26a–26c but can comprise one, two or more than three cover portions. Each cover portion 26a–26c includes a corresponding peripheral-contact surface 28a–28c and a corresponding cover vent 30a–30c that can align with a corresponding frame vent 20a–20c to form a passage between an exterior region and the interior region 16. The vent cover 12 can be located and attached anywhere on the frame 14 such that one or more of the cover portions 26a–26c align with a corresponding frame vent 20a–20c to affect the airflow between an exterior region and the interior region 16. Furthermore, the vent cover 12 can be retained in any of the positions to allow the user to selectively increase or decrease the level of airflow between an exterior region and the interior region 16.

The first position (not shown in FIG. 1) can be defined by substantially all of each peripheral-contact surface 28a–28c contacting corresponding frame-vent perimeters 22a–22c to inhibit air flow between the peripheral contact surface 28a–28c and frame vent perimeters 22a–22c. In the first position thus defined, air can still flow through the frame vents 20a–20c. If desired, air can also flow through discontinuities between the peripheral-contact surfaces 28a–28c and frame-vent perimeters 22a–22c. As shown in FIG. 2B, air can also flow through a portion of the frame vents 20a–20c that are not covered by the cover portions 26a–26c, or between an exterior region and the interior region 16 otherwise as desired. Thus, in some embodiments, a portion of each peripheral-contact surface 28a–28c may contact a portion of a corresponding frame-vent perimeter 22a–22c, or substantially all of each peripheral-contact surface 28a–28c may contact a portion of a corresponding frame-vent perimeter 22a–22c, to permit a substantially non-zero first level of air flow through the frame vents 20a–20c when the vent cover 12 is in the first position. In other embodiments, the peripheral contact surfaces 28a–28c can contact corresponding frame-vent perimeters 22a–22c to form a substantially air tight seal. Consequently, the first position can be defined such that the first level of airflow through the frame vents 20a–20c is zero or substantially zero.

In the second position, as shown in FIGS. 1 and 2A, the cover portions 26a–26c and frame 14 are moved away from each other relative to their respective locations in the first position, such that a substantially greater level of airflow occurs, which means that a significant difference in ventilation through the frame vents 20a–20c is permitted. In some embodiments, the second position can be defined by substantially all of each peripheral-contact surface 28a–28c not contacting a corresponding frame-vent perimeter 22a–22c such that significant amounts of air can flow between an exterior region and the interior region 16 through the frame vents 20a–20c. In the second position substantially all of each peripheral-contact surface 28a–28c can be a same, substantially constant distance, or a first distance, away from a corresponding frame-vent perimeter 22a–22c. The peripheral-contact surfaces 28a–28c can also be varying distances away from corresponding frame-vent perimeters 22a–22c, for example, discretely varying distances, continuously varying distances, or both, as desired. The varying distances of the second position can substantially all be non-zero distances, or a portion of the peripheral-contact surface 28a–28c or other part of the cover portions 26a–26c may continue to contact a corresponding frame-vent perimeter 22a–22c or other portion of the frame 14 regardless of the position. For example, the cover portions 26a–26c may pivot about a portion of corresponding frame-vent perimeters 22a–22c or a portion of the frame 14, or two or more sections of cover portions 26a–26c may pivot about a common axis or separate axes.

Although two different vent-cover positions are discussed, more positions may be included in the goggle 10. Furthermore, the different vent-cover positions can be discrete or continuous, or otherwise as desired. By retaining the vent cover 12 in these various positions relative to the frame 14, the goggle 10 can quickly and easily cross ventilate the interior region 16 and thus can hinder the formation of condensation on the inside surface of the lens 18 or facilitate removal of such condensation.

Referring to FIGS. 1–2B, in this and certain other embodiments, the vent cover portions 26a and 26c comprise filter elements 32a and 32c that cover the cover vents 30a and 30c to filter out dust, snow, ice or other debris that may be suspended in the air in the exterior region. Thus, if desired, in dusty or snowy environments some degree of ventilation can be maintained without exposing a user's eyes to the dust or snow. And, if desired, in humid ambient environments or during strenuous physical activities, a user can move the vent cover 12 to a position that permits filtered and unfiltered airflow to help remove or reduce the possibility of condensation forming on the inside surface of the lens 18. In other embodiments, the filter elements 32a and 32c can cover a portion of the cover portions 26a and 26c.

Still referring to FIG. 1, the vent cover portion 26b comprises a membrane 31 and the frame vent 20b comprises a filter element 33. The membrane 31 covers the cover vent 30b to substantially prevent air flow through the cover vent 30b and can be any desired material that accomplishes this. For example, the membrane can be thermoplastic or rubber. Thus, if desired, in dusty or snowy environments the first level of air flow through the frame vent 20b can be zero or substantially zero. The filter element 33 covers the frame vent 20b to filter out dust, snow, ice or other debris that may be suspended in the exterior region when the vent cover portion 26b is moved away from the frame vent 20b. In other embodiments, the filter element 33 can cover a portion of the frame vent 20b.

In other embodiments of the goggle 10, one of the three cover vents 30a–30c or any combination of two of the cover vents 30a–30c or all three cover vents 30a–30c can be covered by filter elements. Additionally or alternatively, one, any combination of two, or all three cover vents 30a–30c can be covered by a membrane. Furthermore, additionally or alternatively one, any combination of two or all three frame vents 20a–20c can be covered by filter elements. Also, additionally or alternatively one, any combination of two or all three cover portions 26a–26c can have their corresponding cover vents omitted.

Still referring to FIG. 1, the frame vents 20a–20c can be located anywhere along the frame 14, but are typically located around the lens 18 to promote cross ventilation. In this and certain other embodiments, the frame 14 comprises a top frame vent 20a located in a top frame portion 34a, a side frame vent 20b located in a side frame portion 34b and, a bottom frame vent 20c located in a bottom frame portion 34c. Each frame vent 20a–20c includes a corresponding frame-vent perimeter 22a–22c. The vent cover 12 comprises a top cover portion 26a, a side cover portion 26b, and a bottom cover portion 26c, each cover portion 26a–26c including a corresponding peripheral-contact surface 28a–28c. The vent cover is substantially U-shaped and sized to fit over the top, side and bottom frame portions 34a–34c such that the top, side and bottom cover portions 26a–26b are respectively aligned with the top, side and bottom frame vents 20a–20c to cover the frame vents 20a–20c. When the vent cover 12 is in the first position as shown in FIG. 2B, the peripheral-contact surfaces 28a–28c contact corresponding frame-vent perimeters 22a–22c such that substantially all of the air that passes through the frame vents 20a and 20c into the interior region 16 is filtered. The level of airflow through the frame vent 20b is zero or substantially zero. When the vent cover 12 is in the second position as shown in FIGS. 1 and 2A, the peripheral-contact surfaces 28a–28c do not contact corresponding frame-vent perimeters 22a–22c such that air that passes through the frame vents 20a and 20c into the interior region 16 is filtered and unfiltered. The air that passes through the frame vent 20b is filtered. Thus, when the goggle is worn by a user, the user can quickly and easily increase or decrease the ventilation of the goggle by moving the vent cover 12 to one of the positions and retaining the vent cover 12 in the selected position.

In other embodiments, the frame 14 can comprise any combination of two of the frame vents 20a–20c, or more than three frame vents. The vent cover 12 can comprise corresponding cover vents. For example, as discussed elsewhere herein, the frame 14 can comprise a top frame vent 20a and a bottom frame vent 20c. Alternatively, the frame 14 can comprise a side frame vent 20b and either a top frame vent 20a or a bottom frame vent 20c. Furthermore, the vent cover 12 can comprise one or more cover vents that cover a portion of the corresponding frame vents.

Still referring to FIG. 1, the vent cover 12 can be made of any resilient material that can withstand the forces imposed on it by the user when he/she moves the vent cover 12 among the positions and by the environment when a user wears the goggles in windy, hot, bright, or cold environments or any other environment capable of damaging the vent cover 12. The frame 14 can be a goggle frame, for example, the frame of a goggle a skier typically wears when skiing or a motorcyclist typically wears or any other desired goggle. The lens 18 is typically made of any desired light transmissive material that can protect a user's eyes from bright or harmful light as well as debris or other matter suspended in or propelled through the exterior region. Furthermore, the lens 18 can be attached to the frame 14 using any desired technique. For example, the lens 18 can be glued to the frame 14 with any desired adhesive or the lens 18 can be releasably attached to the frame 14 with any desired type of snap or with any desired mechanism that frictionally retains the lens 18 to the frame 14.

Figure 3:
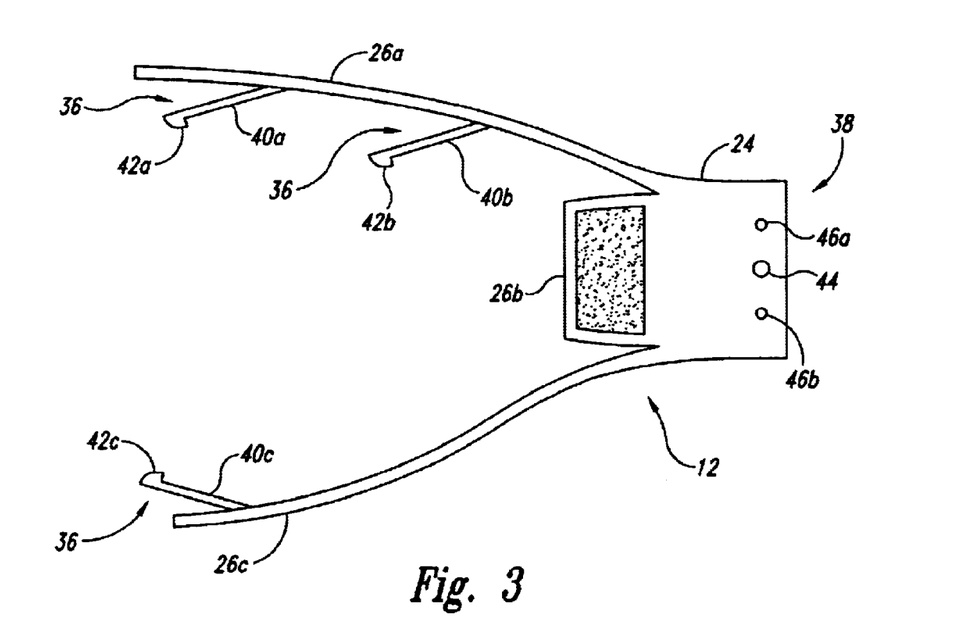
FIG. 3 is a side view of the vent cover included in the goggle of FIG. 1 according to one embodiment of the invention.

FIG. 3 is a side view of the vent cover 12 included in the goggle 10 of FIG. 1 according to one embodiment of the invention. The vent cover 12 can be adjustably attached to the frame 14 by an attachment component 36 that allows the vent cover 12 to move relative to the frame 14 as the vent cover 12 moves among the various positions but substantially prevents the vent cover 12 from being inadvertently removed from the frame 14. The attachment component 36 can comprise, for example, a post or bar with a hook or a ring on one end and attached to the frame 14 or any desired component that permits the vent cover 12 to move relative to the frame 14 but prevents the inadvertent removal of the vent cover 12 from the frame 14. The vent cover 12 can be retained in the various positions relative to the frame 14 by a retention component 38 that allows the vent cover 12 to move relative to the frame 14 as the vent cover 12 moves among the various positions but substantially prevents the vent cover 12 from being inadvertently moved when the vent cover 12 is in one of the various positions. The adjustment component 38 can comprise, for example, a tongue or bar insertable into a slot including detents or any desired component that permits the vent cover 12 to move relative to the frame 14 among the positions but substantially prevents the vent cover 12 from being inadvertently moved out of any of the various positions.

In this and certain other embodiments, the attachment component 36 comprises tongues 40a–40c that extend from the cover portions 26a and 26c and that include corresponding lips 42a–42c, and the retention component 38 comprises a retention post 44 and guide posts 46a and 46b that extend from the body 24. The tongues 40a–40c, retention post 44 and guide posts 46a and 46b can be made of any desired resilient material capable of withstanding, typically without substantially bending, the forces imposed on it by the user and the environment. The tongues 40a–40c can slide within corresponding vent-cover attachment holes (not shown but discussed in greater detail elsewhere herein) to permit movement of the cover portions 26a–26c relative to the frame 14, while the lips 42a–42c substantially prevent the tongues 40a–40c from sliding out of corresponding vent-cover attachment holes. Typically, the tongues 40a–40c are formed as an integral part of the vent cover 12 but can be attached to the vent cover 12 using any desired technique. For example, the tongues 40a–40c can be glued to respective cover portions 26a and 26c using any desired adhesive, or the tongues 40a–40c can be fastened to respective cover portions 26a and 26c using screws. Typically, the lips 42a–42c are integrally formed with the tongues 40a–40c but can be attached to the tongues 40a–40c using the previously discussed techniques or any other desired technique.

The retention post 44 can be inserted into vent-cover retention holes (not shown but discussed in greater detail elsewhere herein) and the guide posts 46a and 46b can be inserted into guide slots (also not shown but discussed in greater detail elsewhere herein) and move within the slots to retain the vent cover 12 in the various positions. Typically, the retention post 44 and guide posts 46a and 46b are integrally formed with the body 24 of the vent cover 12 but can be attached to the body 24 using the previously discussed techniques or any other desired technique. Although the retention post 44 and guide posts 46a and 46b are shown in FIG. 3 protruding from the body 24 in the same direction, in other embodiments, the retention post 44 and guide posts 46a and 46b can protrude from the body 24 in opposite or other desired directions, or one of the guide posts 46a and 46b can protrude from the body 24 in the same direction as the retention post 44 while the other guide post 46a or 46b can protrude from the body 24 in an opposite or other desired direction.

Figure 4A:
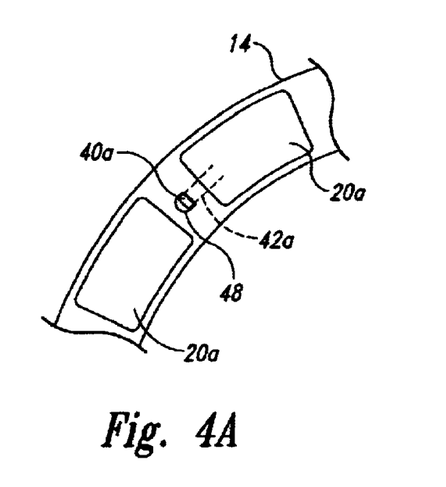
FIG. 4A is a cutaway plan view of the goggle of FIG. 1, illustrating the frame and an attachment component movably attached to the frame.
Figure 4B:
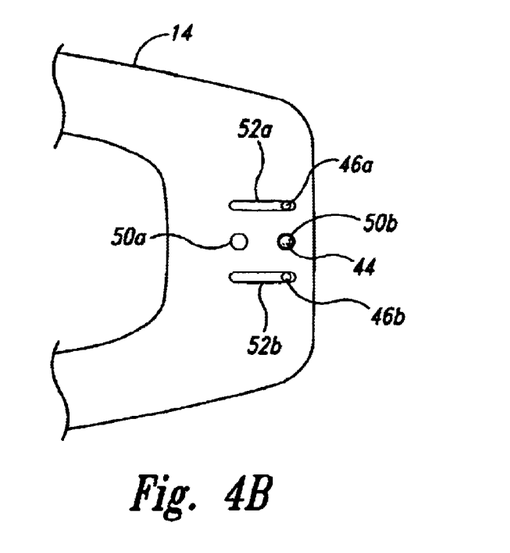
FIG. 4B is a cutaway side view of a side of the goggle of FIG. 1, illustrating the frame and a retention component retaining the vent cover in one of many positions.

FIG. 4A is a cutaway plan view of the goggle 10 of FIG. 1, illustrating the attachment of the vent cover 12 to the frame 14, and FIG. 4B is a cutaway side view of a side of the goggle 10 of FIG. 1, illustrating the retention of the vent cover 12 in the various positions according to one embodiment. FIG. 4A illustrates tongue 40a of the vent cover 12 movably retained in the vent-cover attachment hole 48 to adjustably attach the vent cover 12 to the frame 14. The other tongues and vent-cover attachment holes can be similarly configured. FIG. 4B illustrates the retention post 44 and guide posts 46a and 46b of the vent cover 12 releasably retained in vent-cover retention hole 50b and guide slots 52a and 52b of the frame 14.

Referring to FIG. 4A, the vent cover 12 can be adjustably attached to the frame 14 in any desired manner that permits the vent cover 12 to be moved relative to the frame 14 but does not allow the vent cover 12 to inadvertently be removed from the frame 14. For example, in this and certain other embodiments, the frame 14 comprises a vent-cover attachment hole 48 corresponding to and sized to permit a tongue 40a to slide relative to the frame 14 between the lip 42a and the respective cover portion 26a (not shown) while not permitting the lip 42a to pass through the vent-cover attachment hole 48 without substantial force. Thus, the vent cover 12 can be slidably attached to the frame 14 and moved relative to the frame 14 to the various positions. The vent-cover attachment holes can be located anywhere on the frame 14 that corresponds to the location of the tongues 40a–40c. For example, as shown in FIG. 3, the top cover portion 26a includes two tongues 40a and 40b and the bottom cover portion 26c includes one tongue 40c. Consequently, two vent-cover attachment holes are located adjacent the top frame vent 20a and a third vent-cover attachment hole is located adjacent the bottom frame vent 20c in FIG. 1. In other embodiments, the vent cover 12 may be adjustably attached to the frame 14 by one tongue inserted into a vent-cover attachment hole in a top frame portion and another tongue inserted into a vent-cover attachment hole in a bottom frame portion. Or the vent cover 12 may be adjustably attached to the frame 14 by one or more than three tongues inserted into corresponding vent-cover attachment holes. Furthermore, the vent-cover attachment holes can be located in any desired location on the frame 14 that corresponds to the location of the tongues. In still other embodiments, the tongues can be located on any other desired structure of the goggle with the vent-cover attachment holes located on another desired structure to correspond to the tongues. For example, the frame 14 can include one or more tongues and the vent cover 12 can include one or more vent-cover attachment holes.

Referring to FIG. 4B, the vent cover 12 can be retained in the various positions in any desired manner that permits the user to move the vent cover 12 among the positions yet retains the vent cover 12 in any of the selected positions. For example, in this and certain other embodiments, the frame 14 comprises a first and second vent-cover retention hole 50a and 50b, respectively, corresponding to the first and second vent cover positions, and two guide slots 52a and 52b located on opposite sides of the vent-cover retention holes 50a and 50b. The vent-cover retention holes 50a and 50b are sized to permit the insertion of the retention post 44 when the vent cover 12 is in one of the positions. The vent-cover retention holes 50a and 50b are located in the side of the frame 14 such that when the retention post 44 is in the vent-cover retention hole 50b, the vent cover 12 is in the second position, and when the retention post 44 is in the vent-cover retention hole 50a, the vent cover 12 is in the first position. The guide slots 52a and 52b are located on the frame 14 to correspond with the guide posts 46a and 46b that slide in the guide slots 52a and 52b as the vent cover 12 moves relative to the frame 14. The guide slots 52a and 52b are sized to permit the guide posts 46a and 46b to move in substantially two directions that correspond to the vent cover 12 moving among the two positions. As the user moves the vent cover 12 among the positions, the retention post 44 is moved from the vent-cover retention hole 50a to the vent-cover retention hole 50b and vice-versa, and the guide posts 46a and 46b move in the guide slots 52a–52b. Thus, as the user moves the vent cover 12 from one position to the other and the retention post 44 is not inserted into either vent-cover retention hole 50a or 50b, the guide posts 46a and 46b prevent the vent cover 12 from moving in a direction other than toward the vent-cover retention holes 50a or 50b.

In some embodiments, the guide posts 46a and 46b do not necessarily have to be located adjacent the retention post 44 of the vent cover 12, but rather can be located anywhere on the vent cover 12 or frame 14, as desired, with the guide slots 52a and 52b correspondingly located in the frame 14 to receive the guide posts 46a and 46b. In other embodiments, the retention post 44 and guide posts 46a and 46b can be located on any other desired structure of the goggle 10 with the vent-cover retention holes 50a and 50b and guide slots 52a and 52b located on another desired structure to correspond to the retention post 44 and guide posts 46a and 46b. For example, the frame 14 can include the retention post 44 and guide posts 46a and 46b, and the vent cover 12 can include the vent-cover retention holes 50a and 50b and guide slots 52a and 52b. In still other embodiments, the retention component 38 and attachment component 36 can be the same component. For example, the vent cover 12 can include one or more tongues 40a–40c that include one or more detents sized and located on the one or more tongues 40a–40c to retain the vent cover 12 in the various positions. Or, the guide posts 46a and 46b can include lips 42a and 42b to adjustably attach the vent cover 12 to the frame 14.

Figure 5:
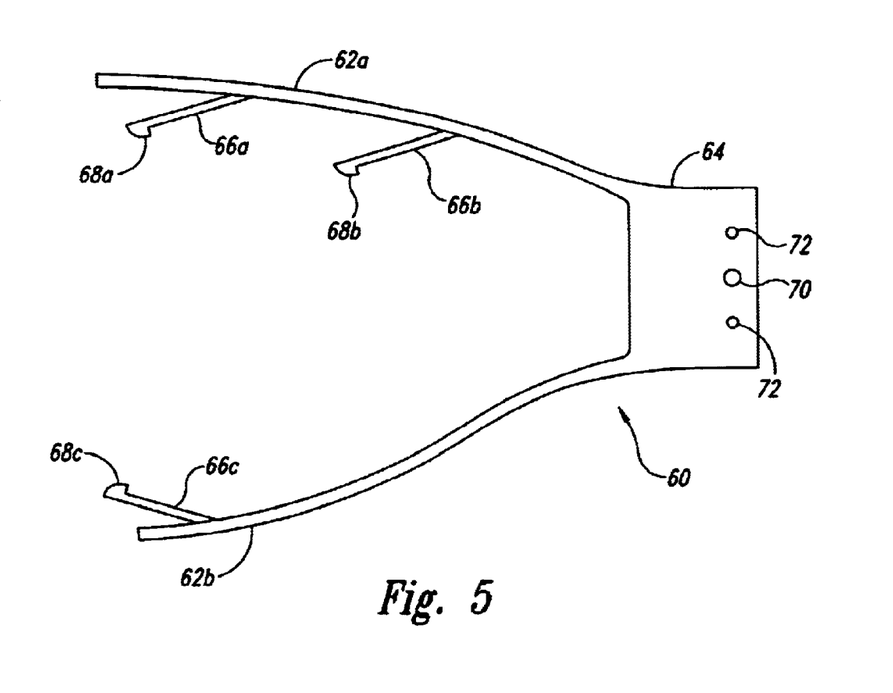
FIG. 5 is a side view of a vent cover according to another embodiment of the invention.

FIG. 5 is a side view of a vent cover 60 according to another embodiment of the invention. In this and certain other embodiments, the vent cover 60 is similar to the vent cover 12 shown in FIGS. 1–4B except the vent cover 60 does not comprise a side cover portion (26b in FIGS. 1 and 3). Thus, the discussion of the vent cover 12 presented elsewhere herein, except for the discussion of the side cover portion, applies to the vent cover 60.

The vent cover 60 can be adjustably attached to a frame (not shown) of a goggle (not shown) and selectively moved between at least two different positions relative to the frame to increase and/or decrease cross ventilation of the goggle. When the vent cover 60 is attached to the frame 14 in FIG. 1, the side frame vent 20b of the frame 14 allows air to pass between the exterior and interior regions when the vent cover 60 is in any of the positions. Thus, some degree of ventilation is provided at all times. When the vent cover 60 is attached to a frame similar to the frame 14 but with the side frame vent omitted, ventilation can be better controlled. Thus, if desired, the vent cover 60 can have cover vents omitted and can substantially prevent cross ventilation of the interior region in one of the positions.

Still referring to FIG. 5, in this and certain other embodiments, the vent cover 60 comprises a top and bottom cover portion 62a and 62b, respectively, that extend from a body 64 to substantially form a U-shaped vent cover 60. The top cover portion typically corresponds to a top frame vent of a frame while the bottom cover portion typically corresponds to a bottom frame vent of a frame. Three tongues, two of them 66a and 66b extending from the top cover portion 62a and one of them 66c extending from the bottom cover portion 62b, are sized to slide within corresponding vent-cover attachment holes in the frame to permit movement of the vent cover portions 62a and 62b relative to the frame. Three lips 68a–68c each corresponding to a respective tongue 66a–66c substantially prevent the tongues 66a–66c from sliding out of the corresponding vent-cover attachment holes. The retention post 70 extends from the body 64 and can be inserted into vent-cover retention holes in a frame (not shown) to retain the vent cover 60 in the various positions. Two guide posts 72 also extend from the body 64 and can be inserted into corresponding guide slots in a frame. When the guide posts 72 are inserted into the guide slots, the guide posts 72 keep the retention posts aligned with the vent cover retention holes so that the vent-cover can be easily moved between the various positions and retained at any of the positions desired.

In other embodiments, the vent cover 60 can comprise a top cover portion and side cover portion with the bottom cover portion omitted. In still other embodiments the vent cover 60 can comprise a bottom cover portion and a side cover portion with the top cover portion omitted. These embodiments may be desired when a high degree of cross ventilation is not desired.

Although the goggle has been described in considerable detail with reference to certain embodiments for purposes of illustration, other embodiments are possible. Therefore the spirit and scope of the appended claims should not be limited to the above description of the embodiments; the present inventions include suitable modifications as well as all permutations and combinations of the subject matter set forth herein.

What is claimed is:

1. A goggle comprising:
   a frame comprising frame vents comprising at least two of the group consisting of a top frame vent, a bottom frame vent and a side frame vent;
   a lens attached to the frame wherein, when the goggle is worn by a user, the lens and frame define an interior region and an exterior region and the frame vents define a passage operable to transmit air between the interior region and the exterior region; and
   a vent cover adjustably attached to the frame and movable relative to the frame between a first position defining a first level of air flow through the frame vents and a second position defining a second, substantially greater level of air flow through the frame vent,
   wherein:
      the vent cover comprises:
         an attachment component comprising a tongue; and
         a retention component comprising a retention post and a guide post; and the frame comprises:
            a vent-cover attachment hole corresponding to and sized to slidably receive the tongue;
            at least first and second vent-cover retention holes corresponding to and sized to receive the retention post such that when the retention post is inserted into the first vent-cover retention hole the vent cover is in the first position and when the retention post is inserted into the second vent-cover retention hole the vent cover is in the second position; and
            a guide slot corresponding to and sized to slidably receive the guide post such that the guide post slides within the guide slot as the vent cover moves among the positions.

2. A goggle comprising:
   a frame comprising frame vents comprising at least two of the group consisting of a top frame vent, a bottom frame vent and a side frame vent;
   a lens attached to the frame wherein, when the goggle is worn by a user, the lens and frame define an interior region and an exterior region and the frame vents define a passage operable to transmit air between the interior region and the exterior region; and
   a vent cover adjustably attached to the frame and movable relative to the frame between a first position defining a first level of air flow through the frame vents and a second position defining a second, substantially greater level of air flow through the frame vent,
   wherein:
      the frame vents comprise a top frame vent located in a top frame portion of the frame and a bottom frame vent located in a bottom frame portion of the frame; and
      the vent cover is substantially U-shaped and comprises:
         a top cover portion slidably attached to the top frame portion; and
         a bottom cover portion slidably attached to the bottom frame portion.

3. A goggle comprising:
   a frame comprising frame vents comprising at least two of the group consisting of a top frame vent, a bottom frame vent and a side frame vent;
   a lens attached to the frame wherein, when the goggle is worn by a user, the lens and frame define an interior region and an exterior region and the frame vents define a passage operable to transmit air between the interior region and the exterior region; and
   a vent cover adjustably attached to the frame and movable relative to the frame between a first position defining a first level of air flow through the frame vents and a second position defining a second, substantially greater level of air flow through the frame vent,
   wherein:
      the frame vents comprise a top frame vent located in a top frame portion of the frame, a side frame vent located in a side frame portion of the frame, and a bottom frame vent located in a bottom frame portion of the frame; and
      the vent cover is substantially U-shaped and sized to fit over the top frame vent, the side frame vent and the bottom frame vent.

4. A goggle comprising:
   a frame comprising frame vents comprising at least two of the group consisting of a top frame vent, a bottom frame vent and a side frame vent;
   a lens attached to the frame wherein, when the goggle is worn by a user, the lens and frame define an interior region and an exterior region and the frame vents define a passage operable to transmit air between the interior region and the exterior region; and
   a vent cover adjustably attached to the frame and movable relative to the frame between a first position defining a first level of air flow through the frame vents and a second position defining a second, substantially greater level of air flow through the frame vent, wherein:
the frame vents comprise a top frame vent located in a top frame portion of the frame, a side frame vent located in a side frame portion of the frame, and a bottom frame vent located in a bottom frame portion of the frame; and
the vent cover is substantially U-shaped and comprises:
a top cover portion slidably attached to the top frame portion;
a side cover portion that contacts the side frame portion when the vent cover is in the first position; and
a bottom cover portion slidably attached to the bottom frame portion.

5. A vent cover sized to fit a goggle, the vent cover comprising:
a body;
a top cover portion that extends from the body and includes a peripheral-contact surface;
a bottom cover portion that extends from the body and includes a peripheral-contact surface;
an attachment component operable to adjustably attach the vent cover to a frame of a goggle; and
a retention component operable to retain the vent cover in at least a first and second position relative to the frame when the vent cover is attached to the frame
wherein the attachment component comprises at least two tongues one of the tongues extending from the top cover portion and the other tongue extending from the bottom cover portion, and each tongue sized to fit into a corresponding vent-cover attachment hole in the frame and to slide within the vent-cover attachment hole when the vent cover moves relative to the frame.

6. A vent cover sized to fit a goggle, the vent cover comprising:
a body;
a top cover portion that extends from the body and includes a peripheral-contact surface;
a bottom cover portion that extends from the body and includes a peripheral-contact surface;
an attachment component operable to adjustably attach the vent cover to a frame of a goggle; and
a retention component operable to retain the vent cover in at least a first and second position relative to the frame when the vent cover is attached to the frame
wherein the retention component comprises:
a retention post extending from the body and sized to fit into at least first and second vent-cover retention holes in the frame when the vent cover is attached to the frame and in one of the positions; and
two guide posts each extending from the body and sized to fit into and to slide within a respective one of two guide slots in the frame when the vent cover is attached to the frame.

7. A vent cover sized to fit a goggle, the vent cover comprising:
a body;
a top cover portion that extends from the body and includes a peripheral-contact surface;
a bottom cover portion that extends from the body and includes a peripheral-contact surface;
an attachment component operable to adjustably attach the vent cover to a frame of a goggle; and
a retention component operable to retain the vent cover in at least a first and second position relative to the frame when the vent cover is attached to the frame
wherein:
the attachment component comprises three tongues each comprising a lip sized and located on the tongue to substantially prevent the tongue from sliding out of the vent-cover attachment hole when the tongue is in the vent-cover attachment hole, wherein two of the tongues extend from the top cover portion and one of the tongues extends from the bottom cover portion; and
the retention component comprises:
a retention post extending from the body and sized to fit into at least first and second vent-cover retention holes in the frame when the vent cover is attached to the frame and in one of the positions; and
two guide posts each extending from the body and sized to fit into and to slide within a respective one of two guide slots in the frame when the vent cover is attached to the frame.

8. A vent cover sized to fit a goggle, the vent cover comprising:
a body;
a top cover portion that extends from the body and includes a peripheral-contact surface;
a bottom cover portion that extends from the body and includes a peripheral-contact surface;
an attachment component operable to adjustably attach the vent cover to a frame of a goggle; and
a retention component operable to retain the vent cover in at least a first and second position relative to the frame when the vent cover is attached to the frame,
further comprising a side cover portion that extends from the body, and wherein the top and bottom covered portions extend from the body such that the vent cover is substantially U-shaped.

9. A method of protecting eyes comprising:
placing a vent cover of a goggle in a first position relative to a frame of the goggle, the frame comprising frame vents comprising at least two of the group consisting of a top frame vent, a bottom frame vent and a side frame vent, the first position permitting a first level of airflow through each frame vent; and
moving the vent cover relative to the frame to a second position that permits a second level of airflow through each frame vent, wherein the second level of airflow is substantially greater than the first level of airflow,
wherein moving the vent cover relative to the frame comprises sliding a tongue of the vent cover within a vent-cover attachment hole included in the frame and sized to receive the tongue.

* * * * *